(12) United States Patent
Godfraind et al.

(10) Patent No.: US 11,471,700 B2
(45) Date of Patent: Oct. 18, 2022

(54) ACTIVE IMPLANTABLE MEDICAL DEVICE HAVING TRANSPARENT ENCAPSULATION

(71) Applicant: Synergia Medical, Mont-Saint-Guibert (BE)

(72) Inventors: Carmen Godfraind, Mont-Saint-Guibert (BE); Pascal Doguet, Mont-Saint-Guibert (BE); Aurélie De Cock De Rameyen, Mont-Saint-Guibert (BE); Aurore Nieuwenhuys, Mont-Saint-Guibert (BE)

(73) Assignee: SYNERGIA MEDICAL, Mont-Saint-Guibert (BE)

( * ) Notice: Subject to any disclaimer, the term of this patent is extended or adjusted under 35 U.S.C. 154(b) by 0 days.

(21) Appl. No.: 17/624,444

(22) PCT Filed: Jul. 16, 2019

(86) PCT No.: PCT/EP2019/069087
§ 371 (c)(1),
(2) Date: Jan. 3, 2022

(87) PCT Pub. No.: WO2021/008688
PCT Pub. Date: Jan. 21, 2021

(65) Prior Publication Data
US 2022/0203120 A1    Jun. 30, 2022

(51) Int. Cl.
*A61N 5/06* (2006.01)
*A61N 1/372* (2006.01)
(Continued)

(52) U.S. Cl.
CPC .......... *A61N 5/0622* (2013.01); *A61N 1/0551* (2013.01); *A61N 1/375* (2013.01);
(Continued)

(58) Field of Classification Search
None
See application file for complete search history.

(56) References Cited

U.S. PATENT DOCUMENTS

| 2010/0262208 A1 | 10/2010 | Parker |
| 2015/0005573 A1 | 1/2015 | Lehmann et al. |
| 2015/0173215 A1 | 6/2015 | Rickert et al. |

FOREIGN PATENT DOCUMENTS

| WO | 2018068807 A1 | 4/2018 |

OTHER PUBLICATIONS

Int'l Search Report for PCT/EP2019/069087, dated Mar. 11, 2020.

*Primary Examiner* — Ankit D Tejani
(74) *Attorney, Agent, or Firm* — Blue Filament Law PLLC

(57) ABSTRACT

An active implantable medical device includes an encapsulation (1) defining an inner space sealingly separated from an outer environment by walls transparent to a given wavelength range. The walls have a first main wall (1a) and a second main wall (1b) facing one another and separated from one another by an inner height (Hi) of the inner space. An encapsulation includes a housing formed by a first component (2) and a second component (3) both made of a single material and hermetically joined to one another along a single interface (23) to define the inner space hermetically sealed by the walls from the outer environment. An inner space contains an electronic, and facing a wall of the encapsulation. wherein joining of the first component and second components (2, 3) is carried out by welding without addition of a third material, the inner space has a volume (Vi) of at least 2 $cm^3$.

20 Claims, 7 Drawing Sheets

(51) Int. Cl.
*A61N 1/375* (2006.01)
*A61N 1/378* (2006.01)
*A61N 1/05* (2006.01)

(52) U.S. Cl.
CPC ....... *A61N 1/3787* (2013.01); *A61N 1/37217* (2013.01); *A61N 5/0601* (2013.01); *A61N 2005/066* (2013.01); *A61N 2005/0626* (2013.01); *A61N 2005/0661* (2013.01); *A61N 2005/0662* (2013.01)

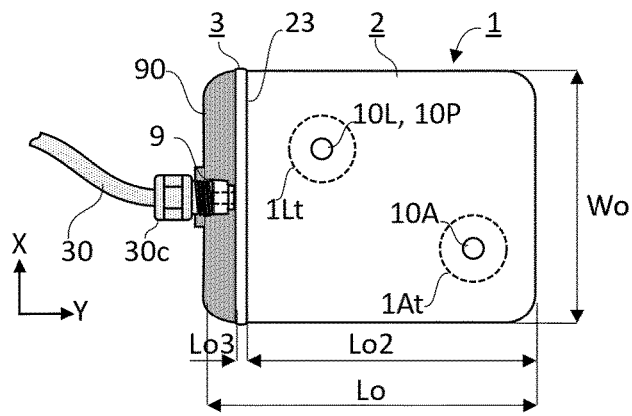
FIG.3(a)
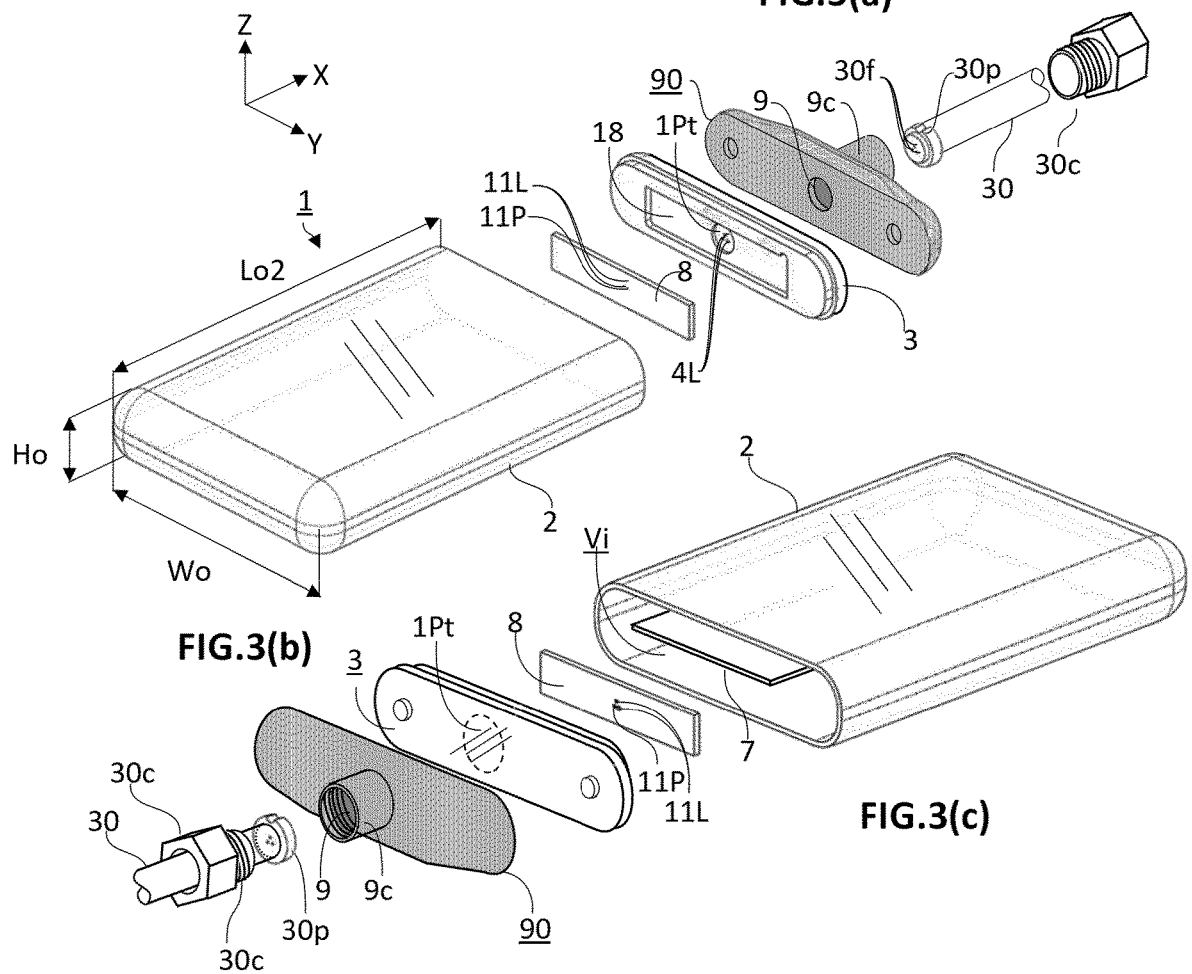
FIG.3(b)
FIG.3(c)

ACTIVE IMPLANTABLE MEDICAL DEVICE HAVING TRANSPARENT ENCAPSULATION

TECHNICAL FIELD

The present invention is in the field of active implantable medical devices (AIMD) for use in medical treatment of a patient. The AIMD of the present invention comprises an encapsulation configured for transmitting light through a skin of the patient or towards a target organ or vessel and/or for receiving optical signals either from outside the patient's body or reflected by the target organ or vessel. The AIMD of the present invention can advantageously further comprise a tissue coupling unit separate from the encapsulation and coupled thereto by means of a lead, for transfer of stimulating pulses between an implantable pulse generator (IPG) enclosed in the encapsulation and the tissue coupling unit and for stimulation of a biological tissue which the tissue coupling unit is coupled to. It is particularly advantageous for an IPG producing optical energy transferred through an optical fibre to a photovoltaic cell comprised in the tissue coupling unit for conversion of optical energy into electric energy for feeding electrode contacts of the tissue coupling unit.

The encapsulation comprises a housing defining an inner volume perfectly sealed from an outer environment and has transparent walls allowing transmission of light energy therethrough. The transparent walls allow communication and data transmission, monitoring of biomarkers, optical power transmission, and the like. For AIMD's comprising a separate tissue coupling unit, transparent walls also allow transmission of optical energy through an optical fibre to an optrode or to a photovoltaic cell converting it into electric energy for feeding electrodes comprised in the tissue coupling unit. The present invention provides perfectly sealed encapsulation housings, transparent to given wavelengths in a variety of geometries, with different shapes and dimensions.

BACKGROUND OF THE INVENTION

Active implantable medical devices (AIMD) have been used for decades for treating a number of disorders, in particular neurological disorders. Active implantable medical devices (AIMD) distinguish from (non-active) implantable medical devices (IMD), like RFID tags and the like, in that AIMD's are configured for actively interacting with the body they are inserted in, such as by stimulating tissues, monitoring of vital signs, and the like. Generally, AIMD's are able to transfer energy from and to the implant. AIMD's therefore generally enclose a source of energy, such as a battery or a rechargeable battery.

A major type of AIMD's consists of neurostimulators, which deliver electrical pulses to a tissue such as a nerve or a muscle for diagnosing or treating a number of disorders such as Parkinson's disease, epilepsy, chronic pain, motor disorders, and many other applications. Depending on the tissue to be treated, the type of electrodes used, and the distance between electrodes, the voltage required between implanted electrodes is generally of the order of 15V±5V. Such voltage requires an electrical pulse generator of such dimensions that electric stimulating implants are generally formed of two separate components: on the one hand, the electrodes which are implanted directly onto the tissue to be treated and, on the other hand, the electrical pulse generator, of larger dimensions, and enclosed in an encapsulation, which can be implanted at various locations in the body depending upon the application. The encapsulation can be implanted in the subclavian region, the lower abdominal area or gluteal region, and the like. The encapsulation is generally made of titanium (alloys) for its mechanical properties and for other reasons, such as biocompatibility and easy processability. Encapsulations made of titanium have, however, low to no transmission to RF, visible and IR wavelengths, and are not MRI-friendly, generating heat and imaging artefacts. Some encapsulations have been made in ceramic materials, opaque to visible and IR lights. Polymers have been tested for encapsulations, but they generally lack durability and resistance to moisture.

In neurostimulators, an energy transfer lead connects the implantable pulse generator (IPG) to a tissue coupling unit, comprising electrodes or an optrode. The energy transfer lead can comprise one or more conductive wires which are generally coiled to provide flexibility, to permit the distance between the electrical pulse generator and the electrodes to be varied and to enhance mechanical stability with a higher compliance with respect to body movements. Because of the use of electric wires, in particular when coiled, such implants can be unsafe to use with magnetic resonance imaging (MRI) apparatuses and also with simple metal detecting portals as used in airports, banks, and the like.

Alternatively, and as described e.g., in WO2016131492, the energy transfer lead can comprise one or more optical fibres transferring optical pulses emitted by the IPG to a photovoltaic cell in the tissue coupling unit converting optical energy into electric energy to feed the electrodes of the tissue coupling unit.

As shown in FIG. 1(a), in its simplest form, a device for delivering energy pulses comprises an implantable pulse generator (IPG) lodged in a housing of an encapsulation, a tissue coupling unit, and an energy transfer lead coupling the tissue coupling unit to the IPG to transmit energy from the IPG to the tissue coupling unit in the form of electrical or optical energy. The IPG can generate electrical pulses transmitted to the electrodes of the tissue coupling unit by conductive wires. Alternatively, and as described, e.g., in EP3113838B1, the IPG can generate light pulses transmitted through optical fibres either to an optrode, or to a photovoltaic cell which transform the light energy into electrical energy which is fed to the electrodes. The term "energy transfer lead" is herein used to define both electric conductors (e.g., wires, tapes) and optical fibres.

In recent years, treatment of tissues with optical energy has shown encouraging potential for the treatment of disorders, either to support the field of optogenetics or using direct infrared light. For such light treatments of a tissue, a so-called optrode can be used. An optrode can be a light emitter focusing a light beam onto a precise area of a tissue, or it can be a light sensor, sensing a reflected, transmitted, or scattered light beam emitted by a light emitter. The light emitter can be powered by electric current in a similar way as the electrodes discussed supra.

Glass housings have been described in respect of so-called smart implants, designed to provide in-vivo diagnostic biofeedback on a patient's condition (blood glucose, intra-ocular pressure, etc.) and/or to measure and transmit diagnostic data, which must function autonomously over its intended lifespan. The company Valtronic advertises an injectable cylindrical glass housing, with outside diameters from 4 mm to 8 mm, wall thicknesses of 0.4-0.6 mm, and lengths from 12 mm to 50 mm. The reduced dimensions of this housing substantially limit the functionalities and the medical applications thereof to monitoring of biomarkers. For example, it is impossible to lodge a battery in such small volume. The geometry (cylindrical) and small dimensions are also motivated by the selection of materials for their production, including borosilicate and bioactive glass (bioglass), quartz, and Kovar glass, which are difficult to shape and/or have limited mechanical resistance.

Alternatively, planar glass housing was also advertised with flat walls made of glass. Again, they are restricted to inner volumes of very small dimensions only suitable for lodging microelectronic circuits.

U.S. Pat. No. 10,251,286 describes an AIMD comprising an encapsulation with a portion of a housing wall forming a window which is transparent to infrared light for communication. The materials selected for the transparent windows are aluminium oxide or aluminium oxide containing ceramic materials, and crystals or gemstones such as sapphire, ruby, diamond, and the like. These materials are very expensive and difficult to shape, thus reducing the available geometries to flat surfaces. Furthermore, this housing is made of several components and of different materials, requiring multiple and sometimes delicate joining operations yielding many joint interfaces, which long term moisture tightness is difficult to ensure.

There is an interest in the art to include more functionalities to AIMD's, including active transfers of energy from and to the implant and, at the same time including monitoring and communication functions. For example, biomarkers such as cardiac pace can be monitored, and parameters of the stimulation pulses can be adapted automatically as a function of the monitored cardiac pace. The latter can be achieved by providing a housing including a wall transparent to given wavelengths, allowing electromagnetic waves, preferably visible and/or infrared light, through the wall. This, however, is only possible in very small dimensions, too small for housing the electronic required for any transfer of energy, or with a number of individual parts made of different materials and soldered together with a soldering metal. This in turn increase production costs and is highly detrimental to the hermeticity of the housing, i.e., it cannot be fully air-; liquid-, and moisture-tight. For example, U.S. Pat. No. 10,251,286 suggests including a desiccant in the housing for reducing the moisture content in the internal volume of the housing.

The present invention proposes an AIMD comprising an encapsulation large enough to house an electronic circuitry comprising opto-electronic components, electronic components, power sources, and the like, required for combining monitoring and communication functions with transfer of energy such as, electric stimulation to an electrode unit coupled to a tissue of a patient. The tightness to air, water, and moisture of the encapsulation housing is excellent by using highly moisture resistant materials and reducing to one the number of interfaces, The encapsulation of the present invention is mechanically resistant and the production thereof is cost-effective, using materials available in large quantities and at reasonable price. These and other advantages are described in more details in the following sections.

SUMMARY OF THE INVENTION

The present invention is defined in the appended independent claims. Preferred embodiments are defined in the dependent claims. In particular, the present invention concerns an active implantable medical device (AIMD) for implantation in a body of a patient. The AIMD comprises an encapsulation defining an inner space of volume (Vi) of at least 2 cm$^3$, sealingly separated from an outer environment by walls defined by an inner surface defining the boundaries of the inner space and by an outer surface in contact with the outer environment. The outer surface is defined by a length (Lo) measured along a first axis (X), a width (Wo) measured along a second axis (Y), and a height (Ho) measured along a third axis (Z) with X⊥Y⊥Z.

the walls of the encapsulation comprise a first main wall and a second main wall facing one another and separated from one another by an inner height (Hi) of the inner space measured along the third axis (Z). The first and second main walls are defined as any wall portion which outer surface is planar or has a single or double curvature of radius of curvature (R) of at least 100 mm and have a mean thickness (t1a, t1b) comprised between 400 and 1200 µm.

The encapsulation comprises a housing formed by a first component and a second component both made of a single transparent ceramic material and hermetically joined to one another along a single interface to define the inner space hermetically sealed by the walls from the outer environment. The inner space contains an electronic circuit board including a main source of light of a given wavelength range and/or a first photodetector for detecting a light of the given wavelength range, wherein the given wavelength range is comprised between 380 and 2200 nm. The interface between the first and second components (2, 3) is formed by welding without addition of a third material, The main source of light and/or the first photodetector) face a light wall portion of the first main wall (1a). The light wall portion has a transmittance to a wavelength of 850 nm at room temperature of at least 75%, measured according to ASTM D1003-7.

In a preferred embodiment, the AIMD is configured for electrically or optically stimulating an electrically or optically excitable tissue of the patient. In this embodiment, the device comprises the following components.

(A) A tissue coupling unit configured for coupling to a human tissue.

(B) An energy transfer lead selected from electrically conductive wires and optical fibres, comprising a distal end configured for coupling to the tissue coupling unit, and a proximal end configured for coupling to the encapsulation.

(C) The encapsulation comprises a connection unit configured for connecting the proximal end of the energy transfer lead to the encapsulation, and encloses in the inner space, a source of optical or electrical energy different from the main source of light and configured for emitting pulses of energy, such that when the proximal end of an energy transfer lead is connected to the connection unit and the distal end of the energy transfer lead is connected to the tissue coupling unit, the energy pulses are transmitted to the tissue coupling unit through the energy transfer lead, and/or a second photodetector different from the first photodetector and configured for detecting light signals emitted from the tissue coupling unit and transferred to the encapsulation through the energy transfer lead comprising an optical fibre, when the proximal end of the optical fibre is connected to the connection unit and the distal end of the optical fibre is connected to the tissue coupling unit.

In this embodiment, it is preferred that the housing encloses the source of optical energy which faces a pulse wall portion facing the connection unit. The pulse wall portion has a thickness preferably comprised between 300 and 1000 µm forming an optical window having a transmittance to a wavelength of 850 nm at room temperature of at least 75% and separating the inner space from the connection unit. The pulse wall portion can comprise one or more micro-optical lenses or prisms integral with the pulse wall portion. The connection unit is preferably integrated in a cover. The energy transfer lead comprises at least one optical fibre and no electric wire, and the encapsulation comprises no feedthrough.

The single transparent ceramic material constituting the first and second components can be selected from: fused silica, borosilicate, spinel, sapphire, or yttrium oxide material. The single material preferably is fused silica.

Depending on the production process used for producing the housing, the surface finish of the walls may not be sufficient to ensure an optimal transmission of the radiations through the light wall portion. In this case, at least a portion of the inner and/or outer surfaces of the first main wall can be polished. To avoid having to polish a larger area than required for transmission of the radiation, it is preferred that the outer and/or inner surfaces of the light wall portion has a surface finish smoother than the surface finish of other portions of the first main wall, and is preferably characterized by an Ra-roughness lower than 3 μm, preferably lower than 1.5 μm, more preferably lower than 1 μm.

The outer surface of the first main wall preferably has an area of at least 3 cm$^2$, preferably at least 5 cm$^2$. The height (Ho) of the outer surface measured along the third axis (Z) between the outer surfaces of the first main wall and of the second main wall can be comprised between 3 and 15 mm, preferably between 5 and 8 mm.

In a preferred embodiment, the inner space encloses an electronic circuitry and the housing is preferably mechanically reinforced by,
  filling the inner space not occupied by the electronic circuitry with a resin, optionally filled with a particulate filler for reducing curing shrinkage, the resin and optional particulate filler being transparent to the given wavelength range, and/or
  providing reinforcing pillars extending over the inner thickness (Hi) of the inner space from the first to the second main walls, the reinforcing pillars being preferably integral with the first and/or second main walls, and/or
  providing walls having a varying thickness reducing a headspace between the electronic circuitry and the inner surface of the walls.

The AIMD can comprise a protective polymeric layer applied over part or all of the outer surface of the encapsulation. Any portion of protective polymeric layer applied over the light wall portion of the first main wall is transparent, yielding a transmittance to a wavelength of 850 nm of both light wall portion and protective polymeric layer together, at room temperature of at least 75%, at least in areas coated over the first and/or additional wall portions. The protective polymeric layer preferably comprises silicone.

An exposed surface of the AIMD is defined by the optional protective polymeric layer applied over part or all of the outer surface as defined supra, by an optional cover, preferably comprising the connection unit, and by any portion of the outer surface of the walls which is not covered by the optional protective polymeric layer or by the optional cover. The exposed surface preferably has a radius of curvature of at least 0.5 mm, preferably at least 1 mm and more preferably at least 2 mm at all points thereof to avoid injuring any tissue surrounding the encapsulation when implanted in a patient's body.

To add functionalities to the AIMD, the light wall portion can comprise one or more micro-optical lenses integral with the light wall portion and facing the main source of light and/or the first photodetector. The AIMD can comprise an additional optical element selected among,
  an additional source of light and/or detector for communication purposes,
  an additional source of light for optical stimulation of a tissue or for optogenetics, and/or
  a monitoring photodetector configured for monitoring bio-markers including one or more of heart beats, blood oxygenation, glucose content in blood, pH levels, blood pressure, feedback from the optical stimulation, and/or
  a photovoltaic cell for charging a battery (12) by irradiation thereof with a source of light positioned outside the patient body, wherein
The additional optical element faces an additional wall portion which can be different from or same as the light wall portion. The additional wall portion preferably has a transmittance to a wavelength of 850 nm at room temperature of at least 75%. It can also comprise one or more micro-optical lenses) integral with the additional wall portion. The thickness of the additional wall portion is preferably comprised between 400 and 1000 μm.

The present invention also concerns a process for producing an active implantable medical device as defined supra. The process comprises the following steps:
  (a) providing a 3D computer assisted design of the first and second components;
  (b) providing a first and second basic blocks of a same transparent ceramic material for each of the first and second components, the transparent ceramic material being transparent to wavelengths comprised between 380 and 2200 nm, and of dimensions suitable for forming the corresponding first and second components by removal of excess material;
  (c) removing excess material from the first and second basic blocks to yield the first and second components either
    mechanically by machining the first and second basic blocks, and/or
    physio-chemically by
      selectively treating with a laser the excess material to be removed from each of the first and second basic blocks such as to obtain a first and second laser treated blocks, wherein the thus laser treated excess material is rendered more sensitive to an etching treatment,
      etching the first and second laser treated blocks with a chemical composition such as to remove the laser treated excess material from the laser treated blocks and not affecting the material not selectively treated by laser, thus obtaining the first and second components, and
  (d) rigidly mounting in the first component the main source of light and/or the first photodetector and additional electronic components, collectively referred to as electronic circuitry,
  (e) forming the housing by sealingly joining the first and second components, thus defining the inner space sealingly separated from the outer environment and enclosing the electronic circuitry such that the main source of light or the photodetector faces the inner surface of the light wall portion of the first component.

Joining is preferably carried out by welding without addition of a third material, preferably by laser welding, more preferably by short or ultrashort pulsed laser welding.

The transparent ceramic material is preferably fused silica. The outer and/or inner surface of the light wall portion can be polished to yield an Ra-roughness lower than 3 μm, preferably lower than 1.5 μm, more preferably lower than 1 μm.

BRIEF DESCRIPTION OF THE FIGURES

For a fuller understanding of the nature of the present invention, reference is made to the following detailed description taken in conjunction with the accompanying drawings in which:

FIG. 3: shows a second embodiment of encapsulation according to the present invention, (a) top view, (b) exploded view from a rear, (c) exploded view from a front of the encapsulation.

DETAILED DESCRIPTION OF THE INVENTION

Figure 1A:
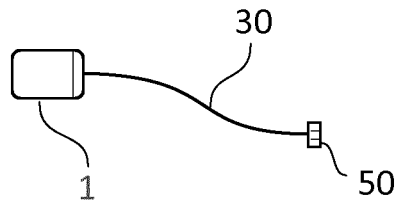
FIG. 1: shows (a) an AIMD according to the present invention, (b) a top view of the encapsulation of the AIMD of FIGS. 1(a), and (c)&(d) side views of two embodiments of the encapsulation of the AIMD of FIG. 1(a).
Figure 1B:
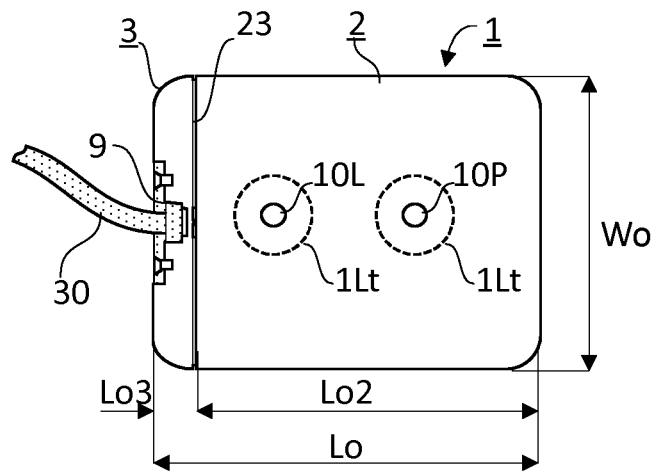

The present invention concerns an active implantable medical device (AIMD) for implantation in a body of a patient. The AIMD is capable of communicating with an exterior of the body it is implanted in by transmission of electromagnetic radiations of at least a given wavelength range comprised between 380 and 2200 nm (=visible and near-infrared ranges). The AIMD comprises a housing defining an inner space of volume (Vi) sealingly separated from an outer environment by walls defined by an inner surface defining the boundaries of the inner space and by an outer surface in contact with the outer environment. The outer surface is defined by a length (Lo) measured along a first axis (X), a width (Wo) measured along a second axis (Y), and a height (Ho) measured along a third axis (Z) with $X \perp Y \perp Z$.

The inner space encloses an electronic circuitry. The electronic circuitry includes a main source of light (10L) and/or a first photodetector (10P). The main source of light (10L) and/or the first photodetector (10P) face a light wall portion (1Lt) of the first and optionally second main walls, which are transparent to the given wavelength range comprised between 380 and 2200 nm.

Main Source of Light (10L) and First Photodetector (10P) and Optional Additional Optical Elements (10A)

As illustrated in FIG. 1(b), 1(c), 1(d), and 6, the inner space contains an electronic circuit preferably printed on an electronic circuit board (7) (ECB), including a main source of light (10L) of the given wavelength range and/or a first photodetector (10P) for detecting a light of the given wavelength range, wherein the given wavelength range is comprised between 380 and 2200 nm.

The main source of light (10L) faces a light wall portion (1Lt) belonging to the first main wall (1a). In one embodiment the main source of light can be configured for transferring optical data to the outer environment through the light wall portion in the form of a light comprised within the given wavelength range. In another embodiment, the main source of light (10L) can be configured for emitting light through the light wall portion towards a target organ or vessel for monitoring biomarkers, for optical stimulation, or for opto-genetic treatment.

The first photodetector (10P) faces the light wall portion (1Lt). If the housing contains both main source of light (10L) and first photodetector (10P), the light wall portion (1Lt) can define a single closed area within the first main wall. Alternatively, the light wall portion can define two distinct closed areas, both belonging to the first main wall (1a) or a first closed area facing the main source of light belonging to the first main wall, and a second closed area facing the first photodetector belonging the second main wall (1b). The first photodetector can be configured for receiving data in the form of electromagnetic radiations comprised within the given wavelength range, emitted from the outer environment through the light wall portion (1Lt) of the first main wall. The first photodetector can be configured for receiving light reflected from a target organ or vessel upon irradiation by the main source of light.

The main source of light (10L) is advantageously a light emitting diode (LED), or a laser LED. The term "light" is used herein in a broad sense, not limited to visible light. The main source of light (10L) suitable for the present invention should be able to emit a light having a wavelength comprised between 380 and 2200 nm, preferably between 700 and 1550 nm. The light emitted is preferably monochromatic.

The inner space and, in particular the electronic circuit board (7), comprises additional electronic components. All electronic components enclosed in the inner space are collectively referred to as electronic circuitry. The electronic circuitry can comprise a processor or an electronic logic control circuit configured for taking actions in response to electromagnetic signals received by the first photodetector (10P) from outside the encapsulation.

The AIMD of the present invention can comprise one or more additional optical elements (10A) located in the inner space and facing an additional wall portion (1At) of the first or second main walls, which can be different from or same as the light wall portion (1Lt). The additional optical element (10A) can be selected among the following:
- an additional source of light and/or detector for communication purposes, and/or
- a monitoring photodetector different from or same as the first photodetector (10P), configured for monitoring bio-markers including one or more of heart beats, blood oxygenation, glucose content in blood, pH levels, blood pressure; light is emitted towards a tissue or organ from the inner space and the light reflected thereby received by the monitoring photodetector is indicative of the values of a given bio-marker, and/or
- an additional source of light for optical stimulation of a tissue or for optogenetics, and/or
- one or more photovoltaic cells for charging a battery (12) by irradiation thereof with a source of light positioned outside the patient body.

The additional wall portion (1At) of the first or second main walls (1a, 1b) preferably has a transmittance to a wavelength of 850 nm at room temperature of at least 75%. It can be provided with one or more micro-optical lenses (4L) integral with the additional wall portion, as illustrated in FIG. 1(*d*). The additional wall portion has a thickness preferably comprised between 400 and 1000 μm, Encapsulation (1)

The gist of the present invention is the encapsulation (1) protecting the electronic circuitry housed inside the inner space from an outer environment. When the encapsulation is implanted in a patient's body, the outer environment is the interior of the patient's body, which is an aggressive medium, with high levels of moisture. During the whole duration of the implant, which can be, and generally is several years long, the electronic circuitry housed in the encapsulation housing must be protected from moisture and from any contact with any body fluid or gases, the patient's body must be protected from non-biocompatible components of the electronic circuitry housed in the encapsulation. The encapsulation housing must therefore durably seal the inner space from the outer environment. These requirements restrict the choice of materials forming the housing and are a challenge for all coupling operations of different components of the housing, which must ensure a long-time sealed coupling. For example, providing hermetic feedthroughs extending across a wall of the housing and required for conducting electrical energy between the inner space and an energy transfer lead (30) extending in the outer environment, is a real challenge because of the small dimensions of the interface formed between a feedthrough and the housing wall. For this reason, the encapsulation of the present invention preferably does not comprise any feedthrough.

The encapsulation must also allow transmission of electromagnetic radiation within the given wavelength range through a wall thereof, which must therefore be transparent to the given wavelength, which restricts even more the choice of materials forming the housing or imposes the use of a third material which must be coupled to an opening in the housing. As discussed above, any joint is a challenge for sealing reasons.

To fulfil all the foregoing requirements, the encapsulation housing of the present invention comprises a first main wall (1*a*) and a second main wall (1*b*) facing one another and separated from one another by an inner height (Hi) of the inner space measured along the third axis (Z). As illustrated in FIG. 4, the first and second main walls (1*a*, 1*b*) are defined as any wall portion which outer surface is planar (cf. FIG. 4(&)&4(*c*)) or has a single or double curvature of radius of curvature (R) of at least 100 mm, preferably at least 200 mm, more preferably at least 500 mm (cf. FIG. 4(*b*)&4(*d*)). A flat surface has an infinite radius of curvature. The first and second main walls (1*a*, 1*b*) can be parallel to one another.

Long Term Moisture-Tightness of the Housing

The housing is formed by a first component (2) and a second component (3) both made of a single material selected among ceramic materials. The first and second components are hermetically joined to one another along a single interface (23) to define the inner space hermetically sealed by the walls from the outer environment. The first and second components are joined along the single interface (23) by welding without addition of a third material. For example, the first and second components can be joined by laser welding, in particular, by short or ultrashort pulsed laser welding, including nano-, fempto-, or pico-second laser welding. This technique is particularly suitable for, albeit not limited to, first and second components made of fused silica.

The choice of a ceramic material as material for the first and second components (2, 3), and forming a single interface (23) of macroscopic dimensions to join the two components, which is rather easy to execute, without addition of any third material which may behave differently at variations of temperature, pressure, pH, and the like, ensure a perfect long-term sealing of the inner space from the outer environment. Preferably, the housing comprises no feedthrough extending across any wall thereof.

Transmission of IR-Radiations

Transmission of electromagnetic radiation within the given wavelength range is ensured by a proper selection of, on the one hand, the ceramic material forming the first and second components of the housing and, on the other hand, the thicknesses and surface finish of the walls.

The main source of light (10L) and/or the first photodetector (10P) face a light wall portion (1Lt) of the first main wall (1*a*). The light wall portion (1Lt) is an integral part of the first main wall and is therefore made of the same material. The light wall portion has a transmittance to a wavelength of 850 nm at room temperature of at least 75%, measured according to ASTM D 1003-7. This allows sufficient transmission of the electromagnetic radiation of the given wavelength across the wall forming the light wall portion (1Lt). Transmission of a wall depends on various parameters, including the absorption coefficient of the wall material, the thickness of the wall, and the roughness (or rather lack of roughness, or better, the smoothness) of the surfaces of the light wall portion (1Lt). The same applies mutatis mutandis to the additional wall portion (1At) facing any additional optical element (10A) optionally enclosed in the housing.

The first and second main walls have a mean thickness (t1*a*, t1*b*) comprised between 400 and 1200 μm. This thickness range is sufficiently low to ensure the desired transmittance, and sufficiently high to ensure mechanical stability. The mean thickness can be determined by computing the five thickest portions of a main surface, and the five thinnest portions, and averaging the thicknesses over the 10 measurements. The inner thickness can be constant. The boundaries of a main surface are defined wherever the radius of curvature drops below 100 mm.

The light wall portion (1Lt) and the optional additional wall portion (1At) can comprise one or more micro-optical lenses (4L) integral with the light and/or additional wall portions (1Lt, 1At) and facing the main source of light (10L) and/or photodetector (10P) and optional additional optical elements (10A) if present. This allows to focus the radiation on a specific focal point, thus increasing the intensity of the signal or targeting accuracy of a light beam to an organ or vessel.

The single material constituting the first and second components (2, 3) can be selected from: fused silica, borosilicate, spinel, sapphire, or yttrium oxide material. Fused silica is a preferred material for the first and second components (2,3), as it has good mechanical properties, high transmittance, good processability, and can easily be welded by laser welding, and is readily available at a reasonable cost.

Depending on the process for manufacturing the housing as described herein, the surface finish of the first (and second) main wall(s) (2,3) can greatly vary. If the surface finish is sufficient to ensure the desired transmittance, then the light wall portion (1Lt) extends over the whole area of the first main wall (1*a*) without any further operation. If, on the other hand, the surface finish is insufficient to yield the desired transmittance, then at least the outer surface, preferably both outer and inner surfaces of the light wall portion (1Lt) and optionally any additional wall portion (1At) can be polished to locally improve the surface finish. The whole area of the first (and optionally second) main wall(s) can thus be polished. This can be advantageous for enhancing biocompatibility but is more time-consuming and more expensive than if only the light (and optionally any additional) wall portion (1Lt, 1At) is polished over an area smaller than the area of the first main wall (1a). According to the latter embodiment, the outer surface and preferably the inner surface too, of the light wall portion (1Lt) and optionally of any additional wall portion (1At) has/have a surface finish smoother than the surface finish of other portions of the first main wall (1a), and is/are preferably characterized by an Ra-roughness lower than 3 μm, preferably lower than 1.5 μm, more preferably lower than 1 μm. Ra-roughness can be measured according to ISO4287. The same applies mutatis mutandis to the second main wall (1b).

With the present invention, perfectly sealed housings allowing communication with the exterior of the housing by electromagnetic radiations in the given wavelength range can be produced with substantially larger dimensions than hitherto available. The outer dimensions of the encapsulation can be defined by a length (Lo) measured along a first axis (X), a width (Wo) measured along a second axis (Y), and a height (Ho) measured along a third axis (Z) with X⊥Y⊥Z.

With the present invention, encapsulation housings defining a sealed inner space can be produced with inner volumes Vi of at least 2 $cm^3$, preferably at least 5 $cm^3$, more preferably at least 8 $cm^3$, most preferably at least 10 $cm^3$. Encapsulations with inner spaces of volume larger than 15 to 20 $cm^3$ become difficult to implant, as they would bulge out below the skin. The first and second main walls (1a, 1b) can have areas (A1, A2) of at least 3 $cm^2$, preferably at least 6 $cm^2$, more preferably at least 10 $cm^2$, most preferably at least 12 $cm^2$. To make it implantable, the encapsulation is preferably thin. The height (Ho) of the outer surface measured along the third axis (Z) between the outer surfaces of the first main wall (1a) and of the second main wall (1b) is therefore preferably comprised between 3 and 15 mm, preferably between 5 and 8 mm.

It may be necessary to reinforce the mechanical resistance of housings comprising first and second main walls of large areas and low thickness. For example, in an embodiment illustrated in FIG. 1(d), the inner space not occupied by the electronic circuitry can be filled with a resin (41), optionally filled with a particulate filler for reducing curing shrinkage. The resin and optional particulate filler are transparent to the given wavelength range and preferably have similar coefficients of expansion to the transparent ceramic material. Preferred resins (41) include but are not limited to epoxy or silicone.

Figure 6A:
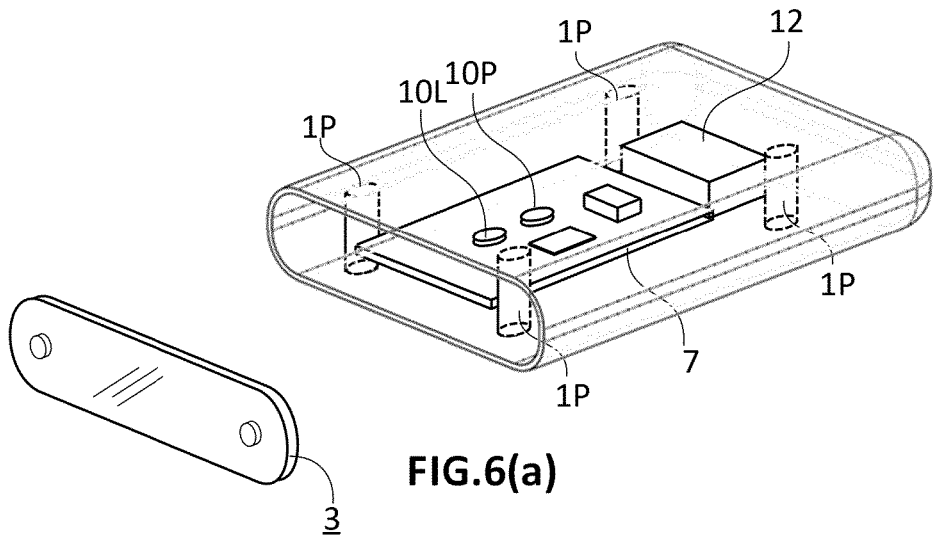
FIG. 6: shows two embodiments of housings containing an electronic circuit board and battery.
Figure 6B:
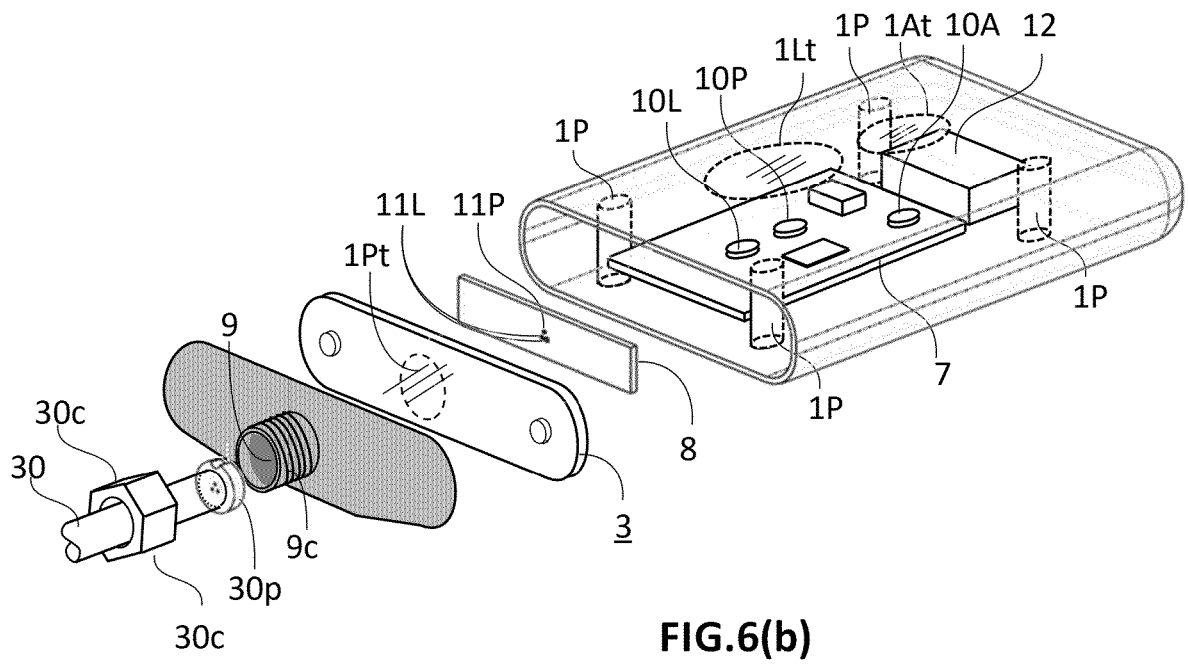

Alternatively, or concomitantly, reinforcing pillars (1P) can be provided, which extend over the inner thickness (Hi) of the inner space from the first to the second main walls (1a, 1b). This is illustrated in FIG. 6(a)&6(b). The reinforcing pillars can be integral with the first and/or second main walls or they can be separate pillars coupled to the first and second main walls by gluing or welding. The coupling of the pillars to the main walls of the housing needs not be hermetic, since they are all comprised within the inner space. For matching the coefficients of thermal expansion (CTE), it is preferred that the pillars (1P) be made of the same transparent ceramic material as the first and second components (2,3) of the housing.

In yet an alternative embodiment, the first and second main walls (1a, 1b) can have a varying thickness reducing a headspace between the electronic circuitry and the inner surface of the walls. The inner surface of the first and second main walls thus mate, at least approximately, the surface topography of the electric circuit board (EBC) (7) defined by the electronic components supported thereon. This solution allows combining portions of main walls with thicker and thinner sections, yielding an overall superior mechanical resistance than a main wall of uniform thickness like the thinner sections.

Encapsulations with the foregoing dimensions are suitable for stimulating AIMD's configured for electrically or optically stimulating a tissue, and can house all the components of the electronic circuitry, including an implantable pulse generator (IPG) and a battery (12) for energizing the IPG, the main source of light (10L) and/or the first photodetector (10P), any additional optical element (10A), and the electronic circuit board (7) housed in the encapsulation (cf. FIG. 6(b)).

Stimulating Pulse AIMD's

In a preferred embodiment illustrated in FIG. 1(a), the AIMD of the present invention is a stimulating AIMD, configured for electrically or optically stimulating an electrically or optically excitable tissue of the patient. In this embodiment, the AIMD comprises:
  the encapsulation (1) as described supra,
  a tissue coupling unit (50) configured for coupling to a human tissue, and
  an energy transfer lead (30) selected from electrically conductive wires and optical fibres (30f), comprising a distal end configured for coupling to the tissue coupling unit, and a proximal end (30p) configured for coupling to the encapsulation (1).

AIMD's Encapsulation (1)

As illustrated in FIGS. 1 to 3, and 6(b), the encapsulation (1) encloses in the inner space,
  an implantable pulse generator (IPG) comprising a source of electrical or optical energy (11L) different from the main source of light (10L) and configured for emitting pulses of energy, such that when the proximal end (30p) of an energy transfer lead (30) is connected to the connection unit (9) and the distal end of the energy transfer lead is connected to the tissue coupling unit (50), the energy pulses are transmitted to the tissue coupling unit through the energy transfer lead (30), and/or
  a second photodetector (11P) different from the first photodetector (10P) and configured for detecting light signals emitted from the tissue coupling unit (50) and transferred to the encapsulation (1) through the energy transfer lead (30) comprising an optical fibre (30f), when the proximal end of the optical fibre is connected to the connection unit (9) and the distal end of the optical fibre is connected to the tissue coupling unit.

Figure 2A:
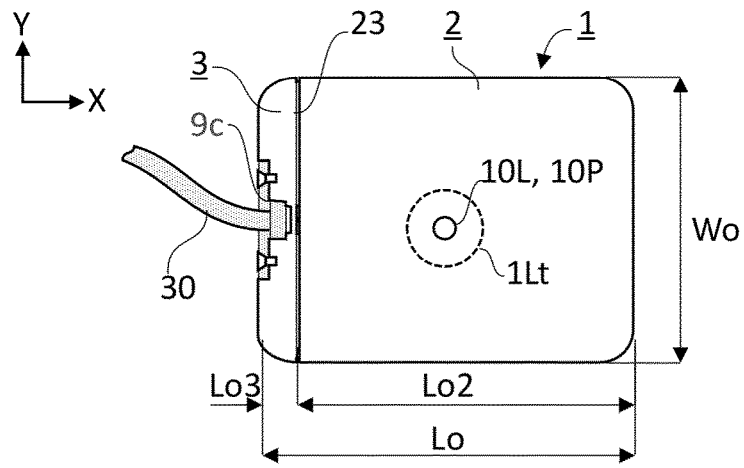
FIG. 2: shows a first embodiment of encapsulation according to the present invention, (a) top view, (b) exploded view from a rear, (c) exploded view from a front of the encapsulation.
Figure 2B:
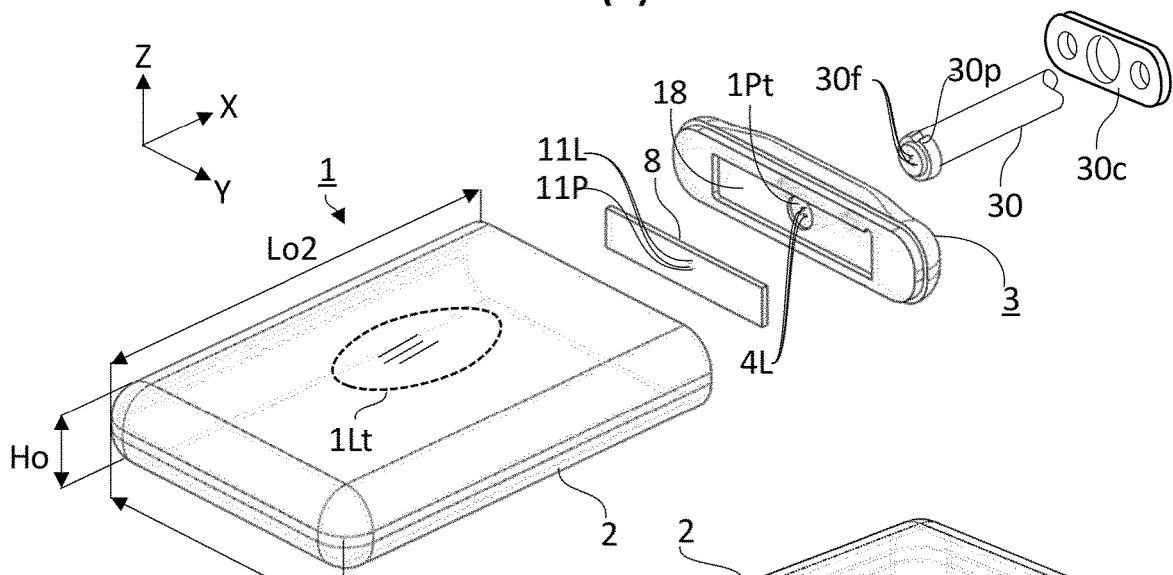

As shown in FIGS. 2&3 and 6(b), the source of optical or electrical energy (11L) and/or the second photodetector (11P) are preferably supported on an IPG electric circuit board (8), which can be the same as, or different from the electric circuit board (7) supporting the main source of light (10L) and/or the first photodetector (10P), depending on the relative orientations of the various sources of light and photodetectors.

Figure 1C:
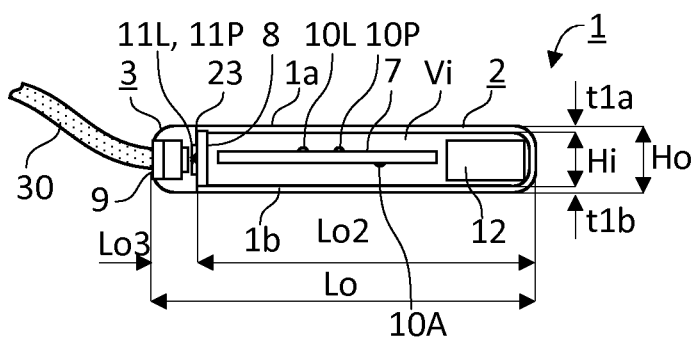
Figure 1D:
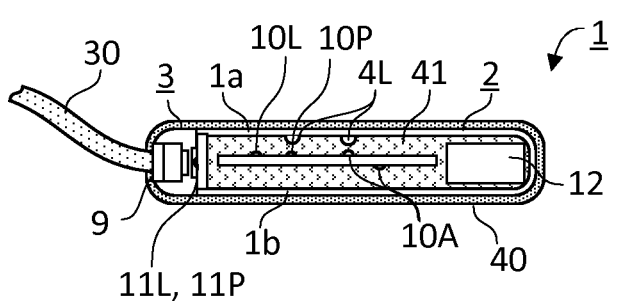

As shown in FIG. 1(c), 1(d), and 6(b), the housing preferably encloses a source of power, which can be a battery (12), preferably a rechargeable battery. A battery can be charged e.g., by inductive or optical power. In the former case, a coil is required preferably lodged in the inner space to avoid the need for feedthroughs to connect it to the battery (12), as well as to reduce the overall volume of the implant. An example of battery charging by inductive power is described in WO2019110378. Charging with optical energy requires the encapsulation to house a photodetector facing an additional wall portion (1At) and in electrical communication with the battery (12).

The encapsulation (1) comprises a connection unit (9) configured for connecting the proximal end (30p) of the energy transfer lead (30) to the encapsulation. The connection unit (9) for connecting the proximal end of an optical fibre (30f) to the encapsulation is particularly critical, because energy transfer losses increase dramatically with any misalignment between the optical fibre and the source of optical energy (11L) and/or the second photodetector (11P). Energy losses must be reduced to a minimum to prolong the autonomy of the battery (12). Examples of connecting units suitable for optimizing the alignment between two implanted optical fibres or between an implanted optical fibre and an implanted source of optical energy are described in PCT/EP2018/073436.

Other connection units (9) are illustrated in FIGS. 2, 3, and 6(b). A lead coupling element (30c) configured for pressing in position the proximal end (30p) of the optical fibre (30f) in the mating encapsulation coupling element (9c). In FIG. 2, the lead coupling element (30c) is in the shape of a plate which can be fixed to a wall of the encapsulation e.g., with two screws, and the encapsulation coupling element (9c) is a cavity mating exactly the geometry of the proximal end (30p) of the optical fibre and threaded cavities for receiving the screws. In FIG. 3, the lead coupling element (30c) is in the shape of a nut comprising an outer thread, mating an inner thread forming the encapsulation coupling element (9c). In FIG. 6(b), the lead coupling element (30c) is in the shape of a nut comprising an inner thread, mating an outer thread on a protruding portion forming the encapsulation coupling element (9c).

The exact geometry of the connection unit (9) is not critical to the present invention, as long as it forms a substantially sealed connection yielding an excellent alignment of the optical fibres (30f) with the source of optical or electrical energy (11L) and/or with the second photodetector (11P). For example, the connection unit (9) can include snap-fitting elements, bayonet, rotate-snap-fitting elements, and the like.

As shown in FIG. 2, the encapsulation coupling element (9c) can be an integral part of the first and/or second components (2, 3). Alternatively, and as discussed more in detail below with reference to FIGS. 3 and 6(b), the encapsulation coupling element (9c) can be formed by or be part of a cover (90) made of a bio-compatible material having sufficient mechanical and ageing resistance in the environment of an implanted AIMD. The cover is preferably made of a polymer but can also be made of metal or of a different ceramic material.

Tissue Coupling Unit (50)

The tissue coupling unit (50) can comprise electrodes coupled to an insulative support, configured for being coupled to the tissue in contact with the electrodes. For example, the tissue coupling unit (50) can be in the shape of, but is not restricted to, a cuff or helical electrode to be wrapped around a target nerve (cf. e.g., WO2019042553 and PCT/EP2018/082703), a rod or needle for deep brain stimulation treatments (cf. e.g., WO2019042553), a two-dimensional array, and the like, all well known in the art. The insulating support comprises an electrode coupling surface, which may contact the tissue to be treated without any stimulating effect thereon. The insulating support is used for securing the electrodes at their treatment positions for long term implantation, and for reducing formation of stray currents. The insulating support is preferably made of a polymeric material. If the insulating material must be deformed for insertion and for accommodating any body movement, it is preferably made of an elastomeric polymer, such as silicone or a polyurethane elastomer. For other electrodes geometries, such as deep brain stimulation electrodes, the insulating support can be rigid and made for example of polyurethane or of an epoxy resin.

The resistance of the tissue is of the order of 3-5 kΩ. With a current of the order of mA, such as 0.1-3 mA, the voltage required between electrodes can be of the order of 10 V.

If the IPG comprises a source of electrical energy (11L), this can be transferred directly to the electrodes by the energy transfer lead (30) comprising a conductive wire. On the other hand, if the IPG comprises a source of optical energy (11L), this can be transferred to the tissue coupling unit (50) by the energy transfer lead (30) comprising an optical fibre (30f). The tissue coupling unit can comprise a photovoltaic cell for converting the optical energy transferred by the optical fibre (30f) into electrical energy to feed the electrodes. Alternatively, the tissue coupling unit can comprise an optrode for stimulating optically a tissue.

Energy Transfer Lead (30)

The energy transfer lead (30) is used to transfer energy from the encapsulation (1) to the tissue coupling unit (50) and back. The energy can be in the form of electrical energy. In this case, the energy transfer lead (30) comprises at least one conductive wire. If the energy is optical energy, the energy transfer lead (30) comprises at least one optical fibre (30f).

It is preferred that the IPG comprises a source of optical energy (11L); the energy transfer lead (30) comprises an optical fibre (30f) and the tissue coupling unit can comprise a photovoltaic cell. The source of optical energy (11L) faces a pulse wall portion (1Pt) of the housing walls positioned vis-n-vis the connection unit (9), and which has the same optical properties as the light wall portion (1Lt). The inner and/or outer surfaces of the pulse wall portion can also be polished to yield smoother surface finish than other portions of the housing, and thus enhance transmittance.

The use of electrically conductive wires is known in the art. Their use is herein not preferred because, on the one hand, the connection of a conductive wire to the IPG lodged in the inner space of the housing requires the use of feedthroughs which are a source of failure because it is very difficult to maintain a seal around the feedthroughs and, on the other hand, because conductive wires interfere with magnetic fields and are a problem with magnetic resonance imaging (MRI) and even with security portals in airports, banks, and some administrative buildings. For these reasons, the use of optical fibres is preferred in the present invention. In case electric current must be transferred across a wall of the housing, it is preferred to use no feedthrough, but through glass vias (TGV), consisting of making a perforation through a wall of the housing, feeling the perforation with a conductive metal, preferably gold or platinum, to form a conductive via, and coupling wires on either sides of the conductive via by any technique known in the art, such as wire bonding, laser bonding, soldering, welding, and the like.

A preferred embodiment of the present invention is therefore a stimulating AIMD defined as follows.

The encapsulation housing encloses the source of optical energy (11L) which faces the pulse wall portion (1Pt) facing the connection unit (9) and having a thickness preferably comprised between 300 and 1000 μm forming an optical window having a transmittance to a wavelength of 850 nm at room temperature of at least 75%. The window separates the inner space from the connection unit, wherein the pulse wall portion optionally comprises one or more micro-optical lenses (4L) integral with the pulse wall portion, as shown in FIGS. 2&3.

The connection unit (9) can be integral with the first or second component (2, 3) as shown in FIG. 2, or can be integrated in a cover (90) as shown in FIGS. 3&6(b).

The energy transfer lead (30) comprises at least one optical fibre (30f), preferably at least two or at least three optical fibres, and no electric wire.

The encapsulation comprises no feedthrough.

The energy transfer lead (30) can comprise a single optical fibre (30f), but it is preferred that it includes more than one optical fibre for adding functionalities to the AIMD. For example, an optical fibre (30f) can be used for transferring optical pulses from the source of optical energy (11L) to a photovoltaic cell included in the tissue coupling unit (50). A second optical fibre can be used to send a feedback signal from a light source included in the tissue coupling unit (50) to the second photodetector (11P) in the encapsulation housing, which feedback signal can be indicative that an electric pulse has been delivered to the tissue it is coupled to. A third optical fibre can be used to activate a recovery circuit in the tissue coupling unit, to prevent damaging side effects. The third optical fibre can transfer optical energy from a recovering source of light emission lodged in the encapsulation housing to a recovery photovoltaic cell to electrically feed the electrodes, thus forming an electrical charge recovering circuit in parallel with the electrical stimulating circuit. A tissue coupling unit comprising a recovery circuit is described e.g., in WO2016131492.

Protective Polymeric Layer (40) and Cover (90)

In a preferred embodiment, the encapsulation (1) can comprise a protective polymeric layer (40) applied over part or all of the outer surface of the housing. Any portion of protective polymeric layer applied over the light wall portion (1Lt) or over the additional or pulse wall portions (1At, 1Pt) of the first and/or second main walls (1a, 1b) must be transparent, yielding a transmittance of at least 75% to a wavelength of 850 nm through the laminate formed by the first or additional wall portion (1Lt, 1At) and the protective polymeric layer (40), at room temperature. At least in areas coated over the first and/or additional wall portions (1Lt, 1At), the protective polymeric layer can comprise a silicone or a parylene. In a preferred embodiment, a protective polymeric layer (40) preferably made of silicone covers a whole area of the encapsulation, as illustrated in FIG. 1(d).

The protective polymeric layer can improve the impact resistance of the housing. It can also have a lubricant effect allowing smoother movements of surrounding tissues relative to the encapsulation. The protective polymeric layer can also reduce growth and attachment of connective tissues on and to the outer surface of the encapsulation.

A protective polymeric layer (40) can be applied over the first and/or second components (2, 3) by any technique known in the art. In one embodiment, the protective polymeric layer is injection moulded separately to form a sheath, which the housing (with or without a cover (90)) is inserted into. The protective polymeric layer can be (injection) moulded over the outer surface of the housing (with or without a cover (90)) positioned in the mould. The protective polymeric layer can be coated over (a portion of) the outer surface of the housing (with or without a cover (90)) by dip coating, spraying, brushing, or the like.

The encapsulation can also comprise one or more covers (90) adding an additional functionality to the encapsulation (e.g., forming the connection unit (9)). A cover is herein defined in any component of the encapsulation, which is distinct from the first and second components (2,3) and having no contact with the inner space. The cover can be made of any biocompatible material including a polymer, metal, or ceramic, depending on the functionality it brings to the encapsulation. It can be applied over a portion of the first and or second components (2,3), either, By moulding, preferably injection moulding, directly over the portion of outer surface of the housing, or By coupling a separately produced cover to the portion of the outer surface of the housing by gluing, soldering, welding, mechanically fitting, and the like.

A cover (90) is advantageous for producing complex shapes which could be more difficult or more expensive to produce with the transparent ceramic material forming the first and second elements (2, 3). The transparent ceramic material forming the first and second components (2, 3) may not necessarily have the most suitable properties to achieve given functionalities. For example, the encapsulation coupling element (9c) of the connection unit (9) can comprise threads or thin walled cavities, and the like (cf. FIG. 2(c)) which can be too brittle if made in the transparent ceramic material. The encapsulation connection unit (9) can therefore be at least partly formed by a cover (90), as illustrated in FIGS. 3 and 6(b). For ensuring an optimal alignment of the cover with the portion of outer surface of the first or second component it must be coupled to, both the cover and the portion can comprise guides in the form of mating protrusions/cavities. If the cover is moulded over the first or second component (1a, 1b), the protrusions can even be mushroom shaped to ensure a mechanical anchoring of the cover to the outer surface of the housing.

Since the cover (90) does not affect the sealing of the inner space, the requirements on the stability to moisture are not as stringent as for the material forming the walls of the housing. If it is used for forming the connection unit (9), the cover must be mechanically stable in time in the aggressive environment of a body and must prevent soiling or degradation of the proximal end of the optical fibre (30f). Furthermore, the polymer must be biocompatible. The cover can be made of a polyaryletherketone, such as PEEK, PEK, PEKK, PEEKK, PEKEKK, an epoxy, a silicone, titanium.

An exposed surface of the encapsulation can be defined as the surfaces in contact with the outer environment, including, the optional protective polymeric layer (40) applied over part or all of the outer surface, a the optional cover (90), e.g., comprising the connection unit (9), and any portion of the outer surface of the walls which is not covered by the optional protective polymeric layer or by the optional cover.

In a preferred embodiment, the exposed surface has a radius of curvature of at least 0.5 mm, preferably at least 1 mm and more preferably at least 2 mm at all points thereof. The absence of sharp edges or sharp corners, i.e., edges or corners having a radius of curvature of less than 0.5 mm, reduces the risks of injury caused by the encapsulation implanted in a body in motion. For example, the second component (3) in FIGS. 3 and 6(b) has sharp edges, but the cover (90) covers these sharp edges and renders the whole exposed surface smooth, i.e., having a radius of curvature of at least 0.5 mm.

Process for Producing an AIMD

Figure 4A:
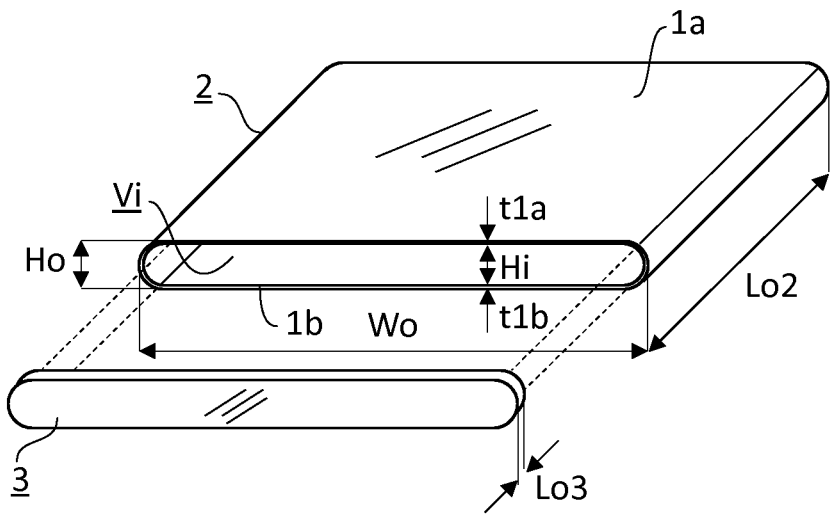
FIG. 4: shows four examples of geometries of an encapsulation housing according to the present invention.
Figure 4B:
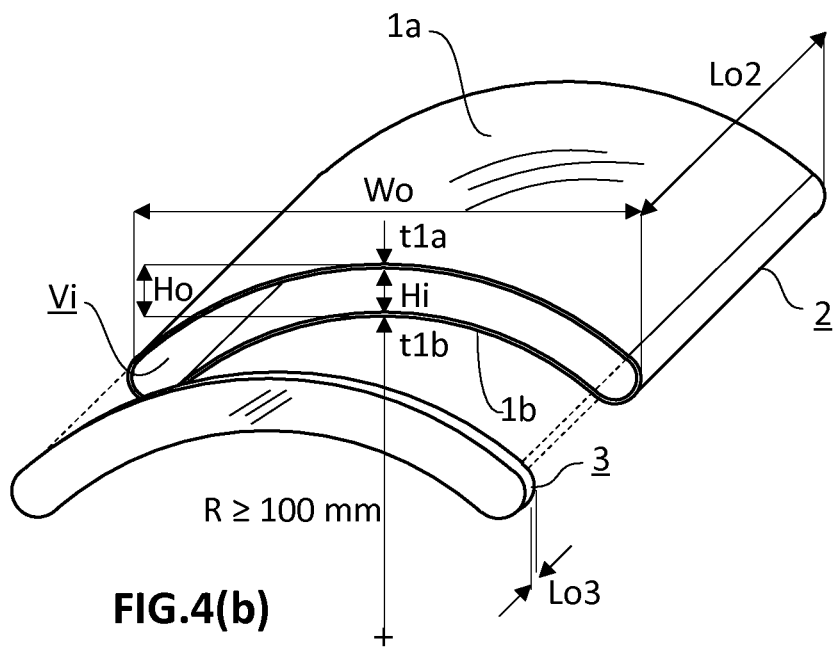
Figure 4C:
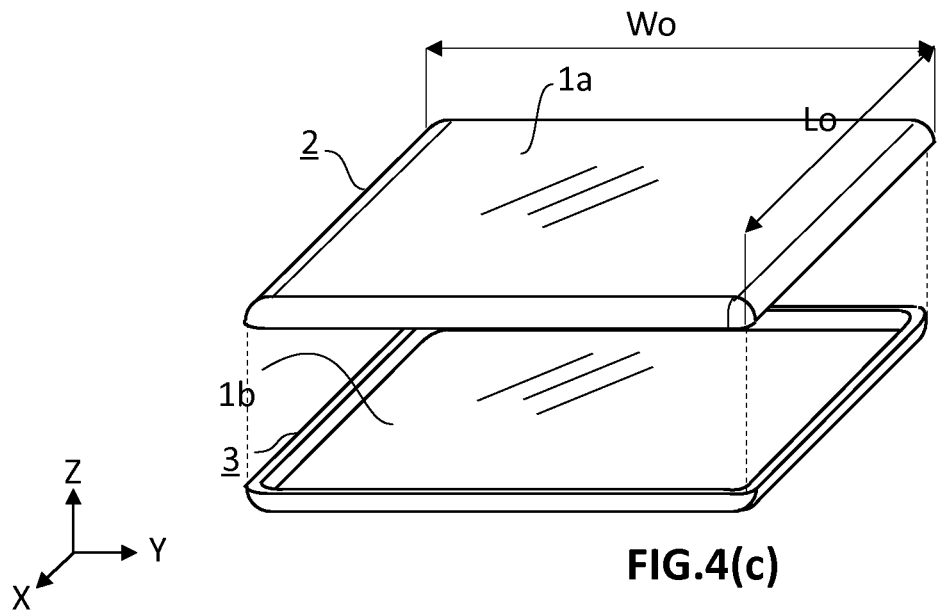
Figure 4D:
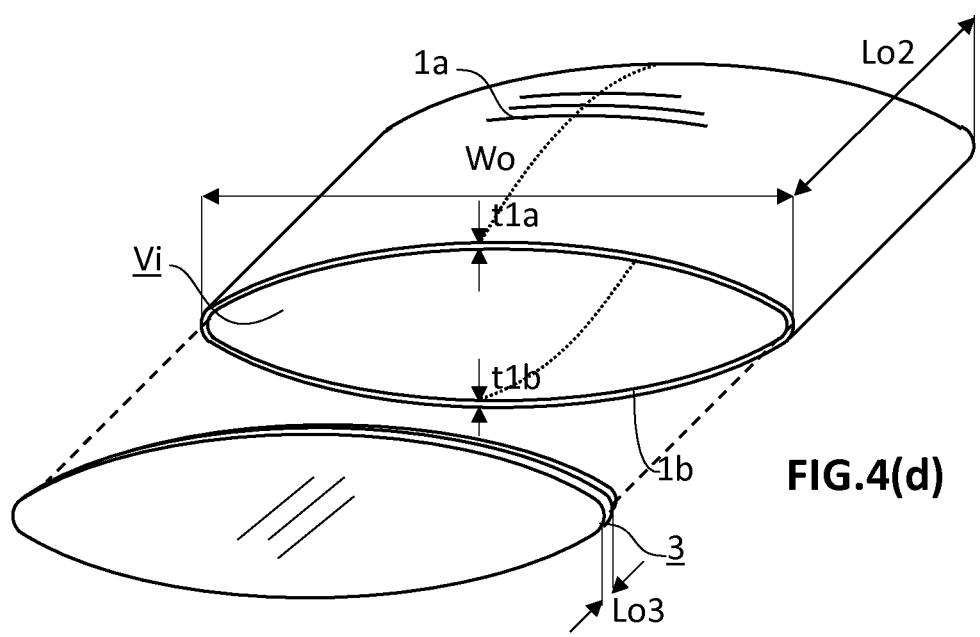
Figure 5A:
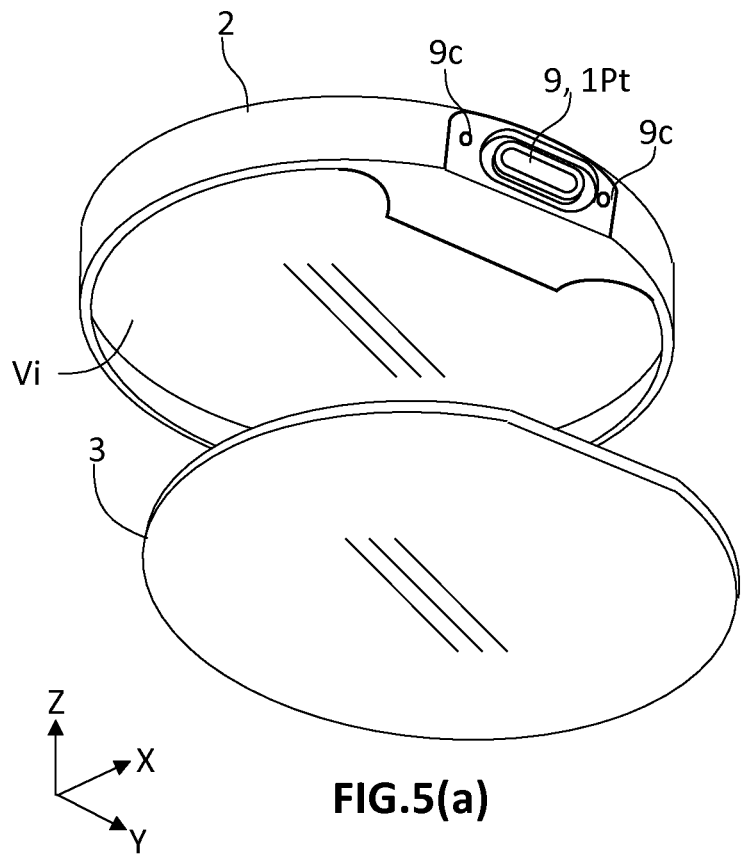
FIG. 5: shows a further example of geometry of an encapsulation housing according to the present invention
Figure 5B:
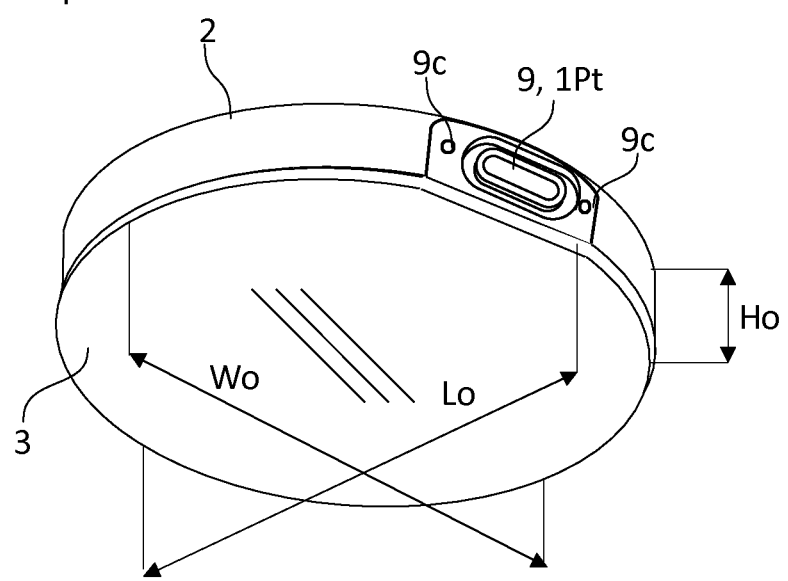

An AIMD according to the present invention can be produced by a process comprising the following steps. First, a 3D computer assisted design (CAD) of the first and second components (1a, 1b) must be provided. Next, a first and second basic blocks are provided, both blocks being made of a same transparent ceramic material for each of the first and second components (1a, 1b). The transparent ceramic material is as defined above, i.e., transparent to wavelengths comprised between 380 and 2200 nm), and is preferably fused silica. The first and second basic blocks must be of dimensions suitable for forming the corresponding first and second components by removal of excess material. The dimensions of the first and second components must allow after joining thereof the formation of a housing of outer dimensions Lo, Wo, and Ho along the first, second and third axes, X, Y, Z. For example, the outer length Lo2 of the first component (2) measured along the first axis (X) can be smaller than Lo as illustrated in FIGS. 1 to 3, and 4(a), (b), and (d), or can be equal to Lo as illustrated in FIGS. 4(c) and 5.

Material in excess is removed from the first and second basic blocks to yield the first and second components (1a, 1b). The main source of light (10L) and/or the first photodetector (10P) and any additional electronic components, collectively referred to as electronic circuitry can be rigidly mounted in the first component and/or second component. The electronic circuitry is preferably supported on one or more electronic circuit boards (7, 8) (ECB). The housing can now be formed by sealingly joining the first and second components, thus defining the inner space sealingly separated from the outer environment and enclosing the electronic circuitry such that the main source of light (10L) and/or the photodetector (10P) face the inner surface of the light wall portion (1Lt) of the first main wall (1a).

Removal of the excess material can be carried out by different techniques. First, excess material can be removed mechanically by machining the first and second basic blocks. Parts with high geometrical accuracy can thus be produced by using computer-controlled tools with the 3D CAD's.

Second, excess material can be removed by a physio-chemical process comprising the following steps.
  selectively treating with a laser the excess material to be removed from each of the first and second basic blocks such as to obtain a first and second laser treated blocks, wherein the thus laser treated excess material is rendered more sensitive to an etching treatment, followed by
  etching the first and second laser treated blocks with a chemical composition such as to remove the laser treated excess material from the laser treated blocks and not affecting the material not selectively treated by laser, thus obtaining the first and second components.

Figure 2C:
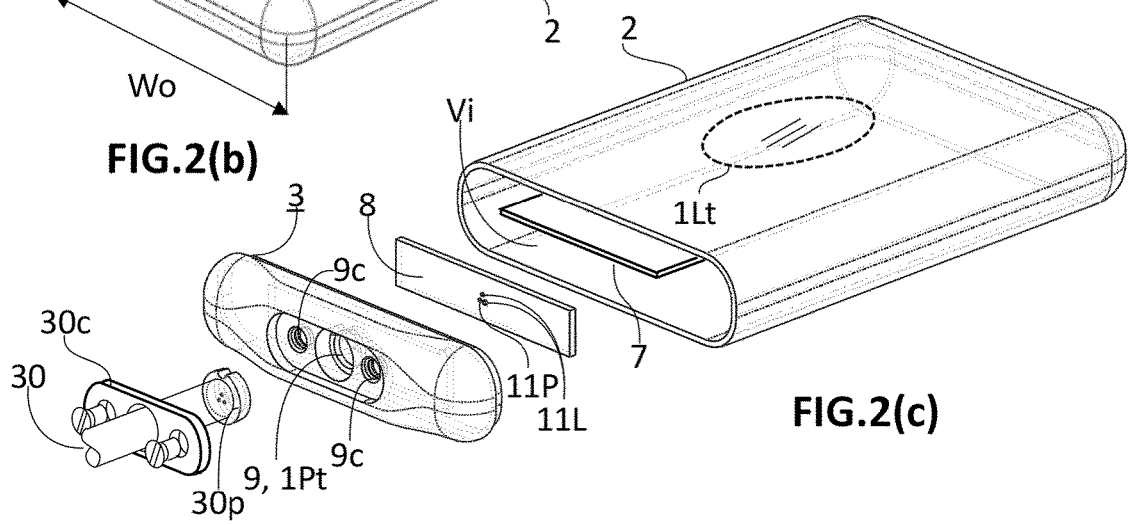

Parts with extremely high definition can be produced with this technique, including threads (e.g., as in FIG. 2(c), #9c), pillars (1P) integral with the first and second main walls (cf. FIG. 6), and the like. Like in FIGS. 3 and 6(b), the second component (3) of the AIMD of FIG. 2 could have been produced with a relatively simple geometry over which a cover (90) would be applied to provide the connection unit (9). As illustrated in FIG. 2, however, the second component (3) has been produced by the physio-chemical process described supra on a block of fused silica, including the thin threads (9c) with excellent accuracy.

Sealingly joining the first and second components (2, 3) is carried out by welding without addition of a third material, preferably by laser welding, more preferably by short or ultrashort pulsed laser welding, including nano-, fempto-, or pico-second laser welding. This technique yields excellent results with fused silica as the transparent ceramic material.

The surface finish of the outer and/or inner surfaces of the light wall portion (1Lt) of the first main wall (1a) may not be sufficiently smooth to optimize transmittance. If required, the outer and/or inner surfaces can be polished by techniques well-known in the art to yield an Ra-roughness lower than 3 µm, preferably lower than 1.5 µm, more preferably lower than 1 µm.

Summary and Advantages

The AIMD of the present invention provides an encapsulation housing sealing extremely well the inner space thereof, containing a number of moisture sensitive components of the electronic circuitry, including a main source of light (10L) and/or a first photodetector (10P) for emission or reception of electromagnetic radiations through the first main wall (1a) of the housing. Transmission of electromagnetic radiations through the first main wall can be used for communicating data to and from the exterior of the patient's body, for optically stimulating a target tissue, for monitoring biomarkers, for charging a battery (12) lodged in the housing, and the like.

The AIMD of the present invention can have large dimensions allowing its use as stimulating AIMD, enclosing a battery (12), a source of optical (or electrical) energy (11L), and/or a second photodetector (11P), as well as a microprocessor for controlling the pulses and information transmitted to and from the encapsulation.

Many functionalities can be included in the AIMD (e.g., additional optical elements (10A), connection unit (9)), either in the inner space or on the outer surface by applying a cover (90) on a portion of the outer wall of the housing.

| Ref# | Reference |
| --- | --- |
| A1 | Surface area of the first main wall 1a |
| A2 | Surface area of the second main wall 1b |
| 1 | Encapsulation |
| 1a | First main wall |
| 1At | Additional wall portion |
| 1b | Second main wall |
| 1Lt | Light wall portion of the first main wall |
| 1P | Reinforcing pillar |
| 1Pt | Pulse wall portion |
| 2 | First component |
| 3 | Second component |
| 4L | Micro-optical lens |
| 7 | Electronic circuit board (ECB) |
| 8 | IPG electronic circuit board |
| 9 | Connection unit |
| 9c | Encapsulation coupling element (for optical fibre 30f) |
| 10A | Additional optical element |
| 10L | Main source of light |
| 10M | Monitoring photodetector |
| 10P | First photodetector |
| 11L | Source of optical or electrical energy |
| 11P | Second photodetector |
| 12 | Battery/power source |
| 18 | Recess for receiving the IPG electronic circuit board (8) |
| 23 | Interface between the first component (2) and the second component (3) |
| 30 | Energy transfer lead |
| 30c | Lead coupling element (for optical fibre 300 |
| 30f | Optical fibre |
| 30p | Proximal end of the energy transfer lead |
| 40 | Protective polymeric layer |
| 41 | Resin filling Vi |
| 50 | Tissue coupling unit |
| 90 | Cover |
| Hi | Inner height of encapsulation along Z |
| Ho | Outer height of encapsulation along Z |
| Lo | Outer length of encapsulation along X |
| Lo2 | Outer length of encapsulation first component along X |

| Ref# | Reference |
|---|---|
| Lo3 | Outer length of encapsulation second component along X |
| t1a | Mean thickness of first main wall |
| t1b | Mean thickness of second main wall |
| Vi | Inner volume of the encapsulation |
| Wo | Outer width of the encapsulation along X |
| R | Radius of curvature |
| X | |
| Y | |
| Z | |

The invention claimed is:

1. An active implantable medical device (AIMD) for implantation in a body of a patient, said AIMD comprising an encapsulation (1) defining an inner space of volume (Vi) sealingly separated from an outer environment by walls defined by an inner surface defining the boundaries of the inner space and by an outer surface in contact with the outer environment, the outer surface being defined by a length (Lo) measured along a first axis (X), a width (Wo) measured along a second axis (Y), and a height (Ho) measured along a third axis (Z) with X⊥Y⊥Z, wherein
 (a) the walls comprise a first main wall (1a) and a second main wall (1b) facing one another and separated from one another by an inner height (Hi) of the inner space measured along the third axis (Z), wherein the first and second main walls are defined as any wall portion which outer surface is planar or has a single or double curvature of radius of curvature (R) of at least 100 mm,
 (b) the encapsulation comprises a housing formed by a first component (2) and a second component (3) both made of a single transparent ceramic material and hermetically joined to one another along a single interface (23) to define the inner space hermetically sealed by the walls from the outer environment,
 (c) the inner space contains an electronic circuit board (7) including a main source of light (10L) of a given wavelength range and/or a first photodetector (10P) for detecting a light of the given wavelength range, wherein the given wavelength range is comprised between 380 and 2200 nm,
Characterized in that, the interface between the first and second components (2, 3) is formed by welding without addition of a third material,
in that, the volume (Vi) of the inner space is at least 2 cm³,
in that, the first and second main walls have a mean thickness (t1a, t1b) comprised between 400 and 1200 µm,
in that, the main source of light (10L) and/or the first photodetector (10P) face a light wall portion (1Lt) of the first main wall (1a), and
in that, the light wall portion (1Lt) has a transmittance to a wavelength of 850 nm at room temperature of at least 75%, measured according to ASTM D1003-7.

2. The active implantable medical device according to claim 1, configured for electrically or optically stimulating an electrically or optically excitable tissue of the patient, said device comprising:
 (d) a tissue coupling unit (50) configured for coupling to a human tissue,
 (e) an energy transfer lead (30) selected from electrically conductive wires and optical fibres (30f), comprising a distal end configured for coupling to the tissue coupling unit (50), and a proximal end (30p) configured for coupling to the encapsulation (1), wherein
 (f) the encapsulation (1) comprises a connection unit (9) configured for connecting the proximal end of the energy transfer lead (30p) to the encapsulation, and encloses in the inner space,
  a source of optical or electrical energy (11L) different from the main source of light (10L) and configured for emitting pulses of energy, such that when the proximal end of an energy transfer lead (30) is connected to the connection unit (9) and the distal end of the energy transfer lead is connected to the tissue coupling unit (50), the energy pulses are transmitted to the tissue coupling unit through the energy transfer lead, and/or
  a second photodetector (11P) different from the first photodetector (10P) and configured for detecting light signals emitted from the tissue coupling unit (50) and transferred to the encapsulation (1) through the energy transfer lead (30) comprising an optical fibre (30f), when the proximal end of the optical fibre is connected to the connection unit and the distal end of the optical fibre is connected to the tissue coupling unit.

3. The active implantable medical device according to claim 2, wherein,
the housing encloses the source of optical energy (11L) which faces a pulse wall portion (1Pt) facing the connection unit (9) forming an optical window having a transmittance to a wavelength of 850 nm at room temperature of at least 75%, and separating the inner space from the connection unit, wherein the pulse wall portion optionally comprises one or more micro-optical lenses (4L) or prisms integral with the pulse wall portion,
the energy transfer lead (30) comprises at least one optical fibre (30f) and no electric wire, and wherein
the encapsulation comprises no feedthrough.

4. The active implantable medical device according to claim 2, wherein the single transparent ceramic material constituting the first and second components (2, 3) is fused silica.

5. The active implantable medical device according to claim 1, wherein the single transparent ceramic material constituting the first and second components (2, 3) is selected from: fused silica, borosilicate, spinel, sapphire, or yttrium oxide material.

6. The active implantable medical device according to claim 5, wherein the outer and/or inner surfaces of the light wall portion (1Lt) has a Ra-roughness lower than 3 µm.

7. The active implantable medical device according to claim 1, wherein the outer and/or inner surfaces of the light wall portion (1Lt) has a surface finish smoother than the surface finish of other portions of the first main wall.

8. The active implantable medical device according to claim 1, wherein, the outer surface of the first main wall has an area (A1), of at least 3 cm².

9. The active implantable medical device according to claim 8, wherein, the area (A1) is at least 5 cm².

10. The active implantable medical device according to claim 1, wherein the height (Ho) of the outer surface measured along the third axis (Z) between the outer surfaces of the first main wall (1a) and of the second main wall (1b) is comprised between 3 and 15 mm.

11. The active implantable medical device according to claim 10, wherein the height (Ho) is between 5 and 8 mm.

12. The active implantable medical device according to claim 1, wherein the inner space encloses an electronic circuitry and wherein the housing is mechanically reinforced by,
filling the inner space not occupied by the electronic circuitry with a resin (41), optionally filled with a particulate filler for reducing curing shrinkage, the resin and optional particulate filler being transparent to the given wavelength range, and/or
providing reinforcing pillars (1P) extending over the inner thickness (Hi) of the inner space from the first to the second main walls (1a, 1b), and/or
providing walls having a varying thickness reducing a headspace between the electronic circuitry and the inner surface of the walls.

13. The active implantable medical device according to claim 1, comprising a protective polymeric layer (40) applied over part or all of the outer surface of the encapsulation, wherein any portion of protective polymeric layer applied over the light wall portion (1Lt) of the first main wall (1a) is transparent, yielding a transmittance to a wavelength of 850 nm of both light wall portion (1Lt) and protective polymeric layer (40) together, at room temperature of at least 75%, at least in areas coated over the first and/or additional wall portions.

14. The active implantable medical device according to claim 13, wherein an exposed surface is defined by the optional protective polymeric layer (40) applied over part or all of the outer surface, by an optional cover (90), and by any portion of the outer surface of the walls which is not covered by the optional protective polymeric layer or by the optional cover, wherein the exposed surface has a radius of curvature of at least 0.5 mm at all points thereof.

15. The active implantable medical device according to claim 13, wherein said protective polymeric layer comprises silicone.

16. The active implantable medical device according to claim 1, wherein the light wall portion (1Lt) comprises one or more micro-optical lenses (4L) integral with the light wall portion (1Lt) and facing the main source of light (10L) and/or the first photodetector (10P).

17. The active implantable medical device according to claim 1, comprising an additional optical element (10A) selected among,
an additional source of light and/or detector for communication purposes,
an additional source of light for optical stimulation of a tissue or for optogenetics, and/or
a monitoring photodetector configured for monitoring bio-markers including one or more of heart beats, blood oxygenation, glucose content in blood, pH levels, blood pressure, feedback from the optical stimulation, and/or
a photovoltaic cell for charging a battery (12) by irradiation thereof with a source of light positioned outside the patient body, wherein
the additional optical element (10A) faces an additional wall portion (1At) different from or same as the light wall portion (1Lt), the additional wall portion,
having a transmittance to a wavelength of 850 nm at room temperature of at least 75%,
optionally comprising one or more micro-optical lenses (4L) integral with the additional wall portion, and
having a thickness preferably comprised between 400 and 1000 µm.

18. A process for producing an active implantable medical device according to claim 1, comprising:
(a) providing a 3D computer assisted design of the first and second components;
(b) providing a first and second basic blocks of a same transparent ceramic material for each of the first and second components (1a, 1b), the transparent ceramic material being transparent to wavelengths comprised between 380 and 2200 nm, and of dimensions suitable for forming the corresponding first and second components by removal of excess material;
(c) removing excess material from the first and second basic blocks to yield the first and second components (1a, 1b) either
mechanically by machining the first and second basic blocks, and/or
physio-chemically by
selectively treating with a laser the excess material to be removed from each of the first and second basic blocks such as to obtain a first and second laser treated blocks, wherein the thus laser treated excess material is rendered more sensitive to an etching treatment,
etching the first and second laser treated blocks with a chemical composition such as to remove the laser treated excess material from the laser treated blocks and not affecting the material not selectively treated by laser, thus obtaining the first and second components, and
(d) rigidly mounting in the first component the main source of light (10L) and/or the first photodetector (10P) and additional electronic components, collectively referred to as electronic circuitry,
(e) forming the housing by sealingly joining the first and second components, thus defining the inner space sealingly separated from the outer environment and enclosing the electronic circuitry such that the main source of light or the photodetector faces the inner surface of the light wall portion (1Lt) of the first component.

19. The process according to claim 18, wherein joining is carried out by welding without addition of a third material.

20. The process according to claim 18, wherein the outer and/or inner surface of the light wall portion (1Lt) is polished to yield an Ra-roughness lower than 3 µm.

* * * * *